United States Patent [19]

Zhang et al.

[11] Patent Number: 5,618,944
[45] Date of Patent: Apr. 8, 1997

[54] METHOD FOR THE SYNTHESIS OF ANTHRAPYRAZOLONES

[75] Inventors: Lin-Hua Zhang, Wilmington, Del.; Joseph Auerbach, Brooklyn, N.Y.

[73] Assignee: The DuPont Merck Pharmaceutical Company, Wilmington, Del.

[21] Appl. No.: 370,933

[22] Filed: Jan. 10, 1995

Related U.S. Application Data

[60] Division of Ser. No. 142,635, Oct. 25, 1993, Pat. No. 5,393,886, which is a continuation-in-part of Ser. No. 57,035, May 9, 1993, abandoned.

[51] Int. Cl.⁶ .................................................. C07D 231/54
[52] U.S. Cl. ............................................................ 548/358.5
[58] Field of Search ............................................ 548/358.5

[56] References Cited

U.S. PATENT DOCUMENTS 4,556,654  12/1985  Showalter et al. .
4,608,439  8/1986  Johnson et al. .
4,672,129  6/1987  Beylin et al. .

FOREIGN PATENT DOCUMENTS 103381  3/1984  European Pat. Off. .
203697  12/1986  European Pat. Off. .
244819  11/1987  European Pat. Off. .

OTHER PUBLICATIONS

G. Zagotto et al., *Bioorganic & Medicinal Chemistry*, 2(7), 1992, p. 659.
H.D. Showalter et al., *J. Med. Chem.*, 27, 1984, p. 255.
H. Showalter et al., *J. Med Chem.*, 30, 1987, p. 121.
W. R. Leopold, *Cancer Research*, 45, 1985, p. 5532.
V. G. Beylin et al., *J. Heterocyclic Chem.*, 26, 1989, p. 85.
Tetrahedron Letters (1985) 26: 157–160.
J. Heterocyclic Chemistry (1985) 23: 1491–1502.

*Primary Examiner*—Robert W. Ramsuer

[57] ABSTRACT

This invention relates to compounds, including 5-chloro-2-[2-[[(4-methylphenyl)sulfonyl]oxy]ethyl]-7-[2,4,6-trimethylphenyl)methoxy]anthra[1,9-cd]pyrazol-6(2H)-one and analogs thereof, which are useful as intermediates for the synthesis of anthrapyrazolone anticancer agents, including losoxantrone. This invention also relates to methods for the synthesis of anthrapyrazolone anticancer agents, including losoxantrone.

7 Claims, No Drawings

METHOD FOR THE SYNTHESIS OF ANTHRAPYRAZOLONES

Cross Reference to Earlier Filed Application

This is a division of application Ser. No. 08/142,635, filed Oct. 25, 1993 now U.S. Pat. No. 5,393,886; which is a continuation-in-part of application Ser. No. 08/057,035, filed May 5, 1993 now abandoned.

FIELD OF THE INVENTION

This invention relates to compounds, including 5-chloro-2-[2-[[(4-methylphenyl)sulfonyl]oxy]ethyl]-7-[2,4,6-trimethylphenyl)methoxy]anthra[1,9-cd]pyrazol-6(2H)-one and analogs thereof, which are useful as intermediates for the synthesis of anthrapyrazolone anticancer agents, including losoxantrone. This invention also relates to methods for the synthesis of anthrapyrazolone anticancer agents, including losoxantrone

BACKGROUND OF THE INVENTION

Losoxantrone is an active drug for the treatment of breast cancer. The published process (Showalter et al., J. Med. Chem. (1987) 30: 121–131; J. Heterocyclic Chem. (1989)26: 85) requires the use of 2-[(hydrazinoethyl)amino] ethanol as a raw material. The limited availability of this raw material makes this published process for the manufacture of losoxantrone impractical. Furthermore, the current process needs a very tedious, costly, and environmentally hazardous chromatographic separation to isolate the desired regioisomer. There is a need, therefore, for improved methods of synthesis of losoxantrone and related compounds. The present invention provides new synthetic processes for the synthesis of losoxantrone and related compounds, which eliminates the need for the use of 2-[(hydrazinoethyl)amino] ethanol and the need for the chromatographic separation of the desired product. Showalter et al., U.S. Pat. No. 4,556,654, issued Dec. 3, 1985 describes the synthesis of anthra [1,9-cd]pyrazol-6(2H)-ones of formulas 1 (losoxantrone) and 2:

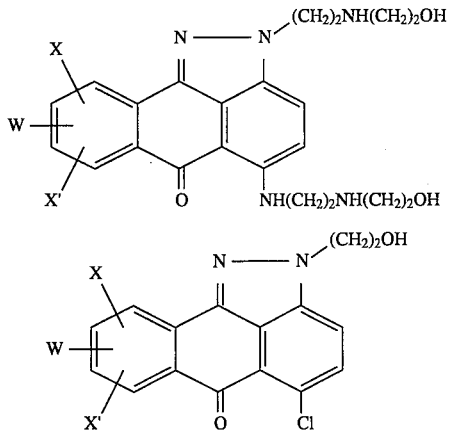

where X, X' and W may be H, OH, alkoxy, or Cl. Showalter et al. also describe the synthetic methods of Schemes A and B shown below.

Scheme A:

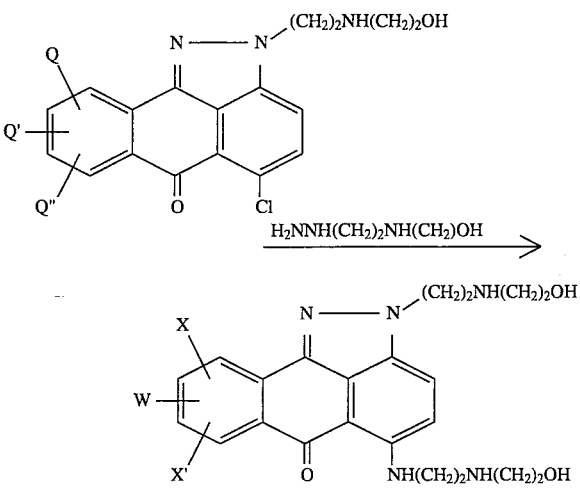

Scheme B:

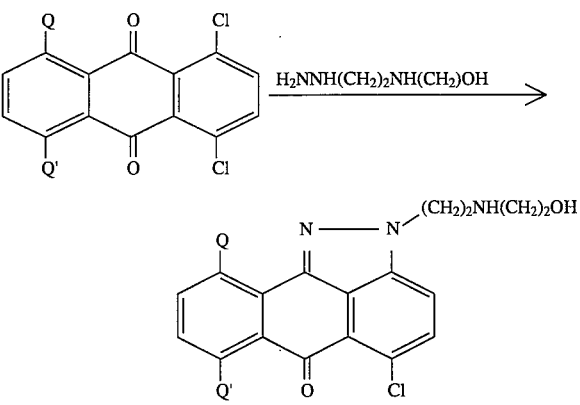

where Q, Q', and Q" are H, alkyl benzyloxy, p-chlorobenzyloxy, or p-methoxybenzyloxy and X, X', and W are defined above.

Johnson and Showalter, U.S. Pat. No. 4,608,439, issued Aug. 26, 1986 describe a process for making anthra[1,9-cd] pyrazol-6(2H)-ones from 1,2-dichloro-5,8-disubstituted-9, 10-anthracenediones and a hydrazine, as shown in Scheme C.

Scheme C:

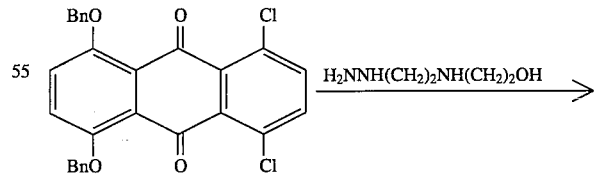

-continued
Scheme C:

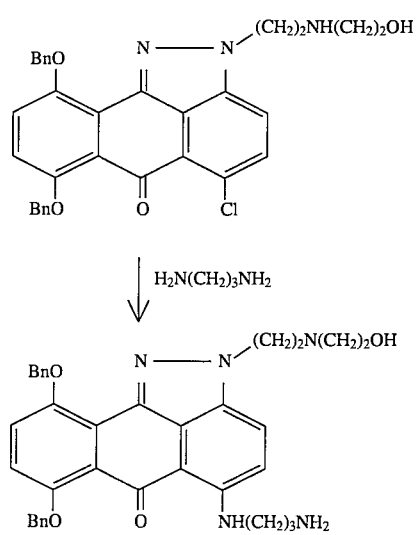

Beylin et al., U.S. Pat. No. 4,672,129, issued Jun. 9, 1987 describe an improved process for the preparation of anthra[1,9-cd]pyrazol-6(2H)-ones from 1,2-dichloro-5,8-disubstituted-9,10-anthracenediones via a chromatographic separation of isomers of formulas 3 and 4, as shown in Scheme D.

Scheme D:

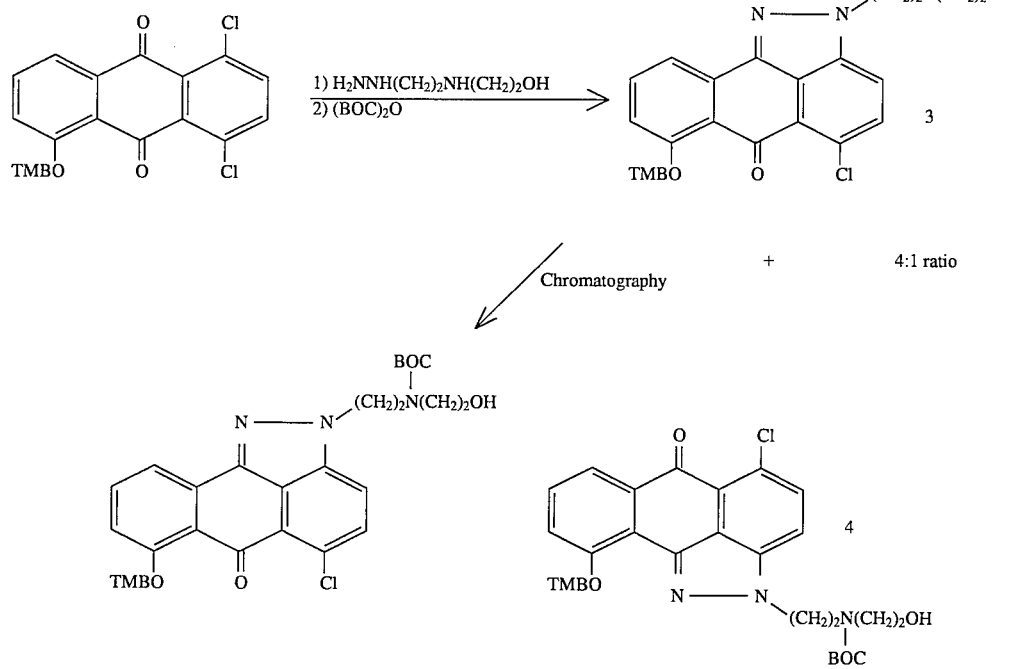

None of the above-cited references describe the methods of the present invention for the synthesis of anthrapyrazolone anticancer agents or the compounds of the present invention which are useful as intermediates for the synthesis of anthrapyrazolone anticancer agents.

SUMMARY OF THE INVENTION

The present invention provides compounds of formula (I) described below, including 5-chloro-2-[2-[[(4-methylphenyl)sulfonyl]oxy]ethyl]-7-[2,4,6-trimethylphenyl)methoxy]anthra[1,9-cd]pyrazol-6(2H)-one and analogs thereof, which are useful as intermediates for the synthesis of anthrapyrazolone anticancer agents, including losoxantrone. This invention also relates to synthetic methods for the preparation of anthrapyrazolone anticancer agents, including losoxantrone.

DETAILED DESCRIPTION OF THE INVENTION

The present invention provides novel anthrapyrazolone derivatives useful as intermediates for the synthesis of anthrapyrazolone anticancer compounds, of formula (I):

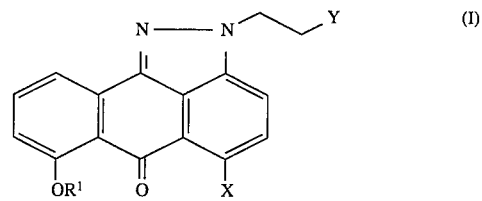

or a pharmaceutically acceptable salt form thereof, wherein:
$R^1$ is H or a hydroxyl protecting group;

X is selected from:
(a) F, Cl, Br, I,
(b) methanesulfonyloxy,
(c) toluenesulfonyloxy,
(d) trifluoromethanesulfonyloxy, or
(e) —OH;

Y is a suitable leaving group, for example but not limited to, those selected from:
 (a) Cl, Br, I,
 (b) —$OSO_2R^2$, or
 (c) —OH;

$R^2$ is selected from:
 (a) $C_1$–$C_4$ alkyl,
 (b) $C_vF_{2v+1}$ where v is 1 to 4, or
 (c) phenyl or phenyl optionally substituted with from 1 to 3 of the groups selected from Cl, F, Br, $NO_2$, —$OR^6$, or $C_1$–$C_4$ alkyl;

$R^6$ is selected from: H, $C_1$–$C_8$ alkyl, $C_2$–$C_6$ alkenyl, $C_3$–$C_8$ cycloalkyl, $C_4$–$C_8$ cycloalkylmethyl, $C_6$–$C_{10}$ aryl, or $C_7$–$C_{11}$ arylalkyl;

with the proviso that when X is Cl, Y can not be —OH.

Preferred compounds of the present invention are compounds of formula (I) wherein:

$R^1$ is selected from:
 (a) benzyl substituted with 0–3 $R^5$;
 (b) naphthylmethyl substituted with 0–3 $R^5$;
 (c) anthrylmethyl substituted with 0–3 $R^5$;
 (d) $C_1$–$C_4$ alkyl; or
 (e) H;

$R^5$ is independently selected from: $C_1$–$C_4$ alkyl, halogen, $OR^6$, $NO_2$;

$R^6$ is independently selected from: H, $C_1$–$C_8$ alkyl, $C_2$–$C_6$ alkenyl, $C_3$–$C_8$ cycloalkyl, $C_4$–$C_8$ cycloalkylmethyl, $C_6$–$C_{10}$ aryl, or $C_7$–$C_{11}$ arylalkyl;

X is selected from:
 (a) F, Cl, Br, I,
 (b) methanesulfonyloxy,
 (c) toluenesulfonyloxy,
 (d) trifluoromethanesulfonyloxy, or
 (e) —OH;

Y is selected from:
 (a) Cl, Br, I,
 (b) —$OSO_2R^2$, or
 (c) —OH;

$R^2$ is selected from:
 (a) $C_1$–$C_4$ alkyl,
 (b) $C_vF_{2v+1}$ where v is 1 to 4, or
 (c) phenyl or phenyl optionally substituted with from 1 to 3 of the groups selected from Cl, F, Br, $NO_2$, —$OR^6$, or $C_1$–$C_4$ alkyl;

with the proviso that when: X is Cl, $R^1$ is H, $C_1$–$C_4$ alkyl, benzyl, p-chlorobenzyl, or p-methoxybenzyl; then Y can not be —OH.

Also included in the present invention are those compounds of formula (I) defined above, with the proviso that when X is Cl, then Y can not be —OH.

Also preferred compounds of the present invention are compounds of formula (I) wherein:

$R^1$ is selected from:
 (a) benzyl,
 (b) p-methoxybenzyl,
 (c) 2,4,6-trimethylbenzyl,
 (d) $C_1$–$C_4$-alkyl, or
 (e) H;

X is selected from:
 (a) F, Cl, Br, I,
 (b) methanesulfonyloxy,
 (c) toluenesulfonyloxy,
 (d) trifluoromethanesulfonyloxy, or
 (e) —OH;

Y is selected from:
 (a) Cl, Br, I,
 (b) —$OSO_2R^2$, or
 (c) —OH;

$R^2$ is selected from:
 (a) $C_1$–$C_4$ alkyl,
 (b) $C_vF_{2v+1}$ where v is 1 to 4, or
 (c) phenyl or phenyl optionally substituted with from 1 to 3 of the groups selected from Cl, F, Br, $NO_2$ or $CH_3$, with the proviso that when: X is Cl; $R^1$ is H, $C_1$–$C_4$ alkyl, benzyl, or p-methoxybenzyl; then Y can not be —OH.

Preferred are those compounds of formula (I) wherein:

X is halogen, and
Y is —$OSO_2R^2$.

More preferred are those compounds of formula (I) wherein:

X is Cl, and
Y is toluenesulfonyloxy.

Also included in the present invention are compounds of formula (I):

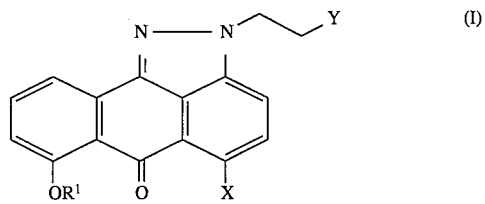

or a pharmaceutically acceptable salt form thereof, wherein:

$R^1$ is selected from:
 (a) benzyl;
 (b) p-chlorobenzyl;
 (c) p-methoxybenzyl;
 (d) $C_1$–$C_4$ alkyl; or
 (e) H;

X is Cl;
Y is —OH.

As used herein, the term "hydroxyl protecting group" means any group known in the art of organic synthesis for the protection of hydroxyl groups. Such protecting groups include, but are not limited to, those listed in Greene and Wuts, "Protective Groups in Organic Synthesis", John Wiley & Sons, New York (1991), the disclosure of which is hereby incorporated by reference. The hydroxyl protecting groups can include, but are not limited to acyl types, aromatic carbamate types and alkyl types. Exemplary are methyl, methoxymethyl, methylthiomethyl, benzyloxymethyl, t-butoxymethyl, 2-methoxyethoxymethyl, 2,2,2-trichloroethoxymethyl, 2-(trimethylsilyl)ethoxymethyl, tetrahydropyranyl, tetrahydrofuranyl, t-butyl, triphenylmethyl, trimethylsilyl, triethylsilyl, t-butyldimethylsilyl, t-butyldiphenylsilyl, pivaloate, N-phenylcarbamate, arylmethyl, substituted arylmethyl, benzyl, substituted benzyl.

The following terms and abbreviations are used herein and are defined as follows. The abbreviation "DMF" as used herein means dimethylformamide. The abbreviation "DMAC" means dimethylacetamide. The abbreviation "DMSO" means dimethylsulfoxide. The abbreviation "TMBO" means trimethylbenzyloxy. The abbreviation "OTs" means toluenesulfonyloxy. The abbreviation "BnO" means benzyloxy.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^5$ and $R^6$) occurs more than one time in any constituent or in any formula, its definition on each occurrence is independent of its definition at every other occurrence. Thus, for example, if a group is shown to be substituted with 0–2 $R^5$, then said group may optionally be substituted with up to two $R^5$ and $R^5$ at each occurrence is selected independently from the defined list of possible $R^5$.

Combinations of substituents and/or variables are permissible only if such combinations result in stable compounds. By stable compound or stable structure it is meant herein a compound that is sufficiently robust to survive isolation to a useful degree of purity from a reaction mixture.

The term "substituted", as used herein, means that one or more hydrogen on the designated atom is replaced with a selection from the indicated group, provided that the designated atom's normal valency is not exceeded, and that the substitution results in a stable compound.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, cycloheptyl, cyclooctyl and adamantyl. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

"Halo" or "halogen" as used herein refers to fluoro, chloro, bromo and iodo.

As used herein, "aryl" or "aromatic residue" is intended to mean phenyl or naphthyl; the term "arylalkyl" represents an aryl group attached through an alkyl bridge.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The reactions of the synthetic methods claimed herein are carried out in a suitable solvent, said suitable solvent generally being any solvent which is substantially nonreactive (except where the solvent also functions as the suitable base, as discussed below) with the starting materials (reactants), the intermediates, or products at the temperatures at which the reactions are carried out, i.e., temperatures ranging from the solvent's freezing temperature to the solvent's boiling temperature. Suitable solvents include aprotic solvents, including but not limited to polar aprotic organic solvents. Suitable solvents useful in the present invention include but are not limited to toluene, pyridine, dimethylsulfoxide (DMSO), N,N-dimethylformamide (DMF), N,N-dimethylacetamide (DMAC), DMSO, diethyl ether, benzene, or tetrahydrofuran. Where desirable said suitable solvent may also function as a suitable base in the synthetic processes of the invention, for example where the suitable solvent/base is pyridine.

The reactions of the synthetic methods claimed herein are preferably carried out in the presence of a suitable base, said suitable base being any of a variety of bases, the presence of which in the reaction facilitates the synthesis of the desired product. Suitable bases may be selected by one of skill in the art of organic synthesis. Suitable bases include, but are not limited to, inorganic bases such as alkali metal, alkali earth metal, thallium, and ammonium hydroxides, alkoxides, phosphates, and carbonates, such as sodium hydroxide, potassium hydroxide, sodium carbonate, potassium carbonate, cesium carbonate, thallium hydroxide, thallium carbonate, tetra-n-butylammonium carbonate, and ammonium hydroxide. Suitable bases also include organic bases, including but not limited to aromatic and aliphatic amines, such as pyridine, N,N-dimethylaminopyridine, a trialkyl amine such as triethylamine, N, N-diisopropylethylamine, 1,5-diazabicyclo[4,3,0]non-5-ene (DBN), 1,4-diazabicyclo[2,2,2]octane (DABCO), 4-dimethylamino pyridine (DMAP), 1,8-diazabicyclo[5.4.0]undec-7-ene (DBU), or tetramethylethylenediamine (TMEDA).

Step 3.

The present invention also provides a method for the synthesis of a compound of formula (I) comprising reacting a compound of formula (II), or a mixture of a compound of formula (II) and a compound of formula (III):

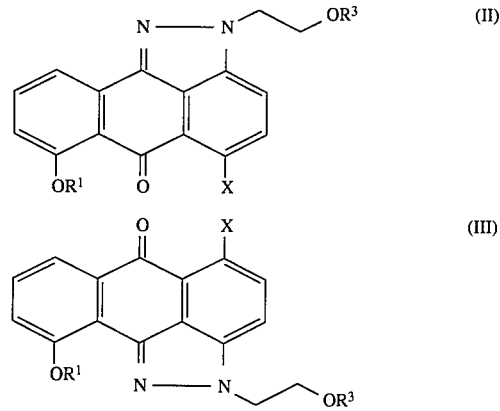

wherein
$R^1$ and X are as defined for formula (I) above and $R^3$ is hydrogen;

with a suitable brominating, chlorinating, or iodinating agent, said reaction being carried out in a suitable solvent, optionally in the presence of a suitable base, to form a compound of formula (I) wherein Y is Br, Cl, or I.

The suitable brominating, chlorinating, or iodinating agent is effective to convert the hydroxyl group in the compound of formula (II) to a Br, Cl, or I group. Such brominating, chlorinating, or iodinating agents are well known in the art of organic synthesis. Examples of such brominating agents include, but are not limited to, triphenylphosphine/carbontetrabromide, HBr, diphos-Br$_2$, N-bromosuccinimide (NBS) and thionyl bromide. Examples of such chlorinating agents include, but are not limited to, triphenylphosphine/carbontetrachloride, HCl, diphos-Cl$_2$, N-chlorosuccinimide (NCS), and thionyl chloride.

By way of general guidance, depending on the solvent, base, and brominating, chlorinating, or iodinating agent selected, the reaction may be carried out at a temperature of about −10 to about 60° C., for about 0.1 to 72 hr, to form a compound of formula (I).

The present invention also provides a method for the synthesis of a compound of formula (I) comprising reacting a compound of formula (II), or a mixture of a compound of formula (II) and a compound of formula (III):

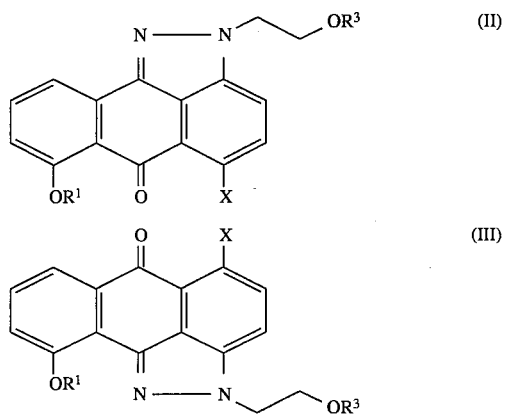

wherein

R$^1$ and X are as defined for formula (I) above and R$^3$ is hydrogen;

with any reagent suitable to convert a hydroxyl group to a leaving group. Such reagent suitable to convert a hydroxyl group to a leaving group can be selected from a variety of such reagents as will be appreciated by one of skill in the art of organic synthesis. Such reagents may be selected from, for example but not limited to, reagents of formula ClSO$_2$R$^2$ wherein R$^2$ is as defined above for formula (I), such as benzenesulfonyl chloride, dimethylbenzenesulfonyl chloride, trimethylbenzene sulfonyl chloride, chlorobenzenesulfonyl chloride, dichlorobenzenesulfonyl chloride, trichlorobenzenesulfonyl chloride, toluenesulfonyl chloride, preferably, toluenesulfonyl chloride (tosyl chloride).

The above reaction is carried out in a suitable solvent, optionally in the presence of a suitable base, to form a compound of formula (I). By way of general guidance, depending on the solvent, base, and reactant selected, the reaction may be carried out at a temperature of about −10 to about 50° C., for about 2 to 72 hours, to form a compound of formula (I). Upon completion of the reaction, the desired product of formula (I) may be isolated from the mixture of isomers in the reaction, for example, by precipitation of the desired compound of formula (I) by addition of an alcohol to the reaction mixture.

The reaction in Step 3 is optionally, but preferably carried out in the presence of a suitable base. Preferable suitable bases are pyridine and 1,8-diazabicyclo [5,4,0]undec-7-ene (DBU). The reaction temperature is generally between about −15° C. and 20° C., preferably a chilled solution. For example, the reaction may be carried out in the presence of DBU at a temperature ranging from about −10° C. to 10° C. for about 3 to 5 hours The reaction in Step 3 may alternatively be carried out, for example, in the presence of pyridine, at a temperature ranging from about −10° C. to 25° C., for about 24 to 60 hours. Other suitable bases can be employed, such as 1,5-diazabicyclo[4,3,0]non-5-ene (DBN), 1,4-diazabicyclo[2,2,2 ]octane (DABCO), 4-dimethylamino pyridine (DMAP), or tetramethylethylenediamine (TMEDA).

Step 2.

The present invention provides a process for the synthesis of a compound of formula (II) and (III), as defined above, comprising reacting 2-hydroxyethylhydrazine with a compound of formula (IV):

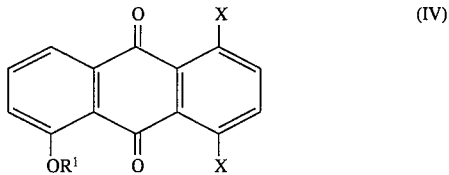

wherein

R$^1$ and X are as defined as above, said reaction being carried out in a suitable solvent, optionally in the presence of a suitable base, to form a compound of formula (II) or (III). The suitable solvent is preferably DMF, DMAC, or DMSO, and is most preferably DMAC. The suitable base is preferably potassium carbonate, sodium carbonate, potassium bicarbonate, sodium bicarbonate, N,N-dimethylaminopyridine, or a trialkylamine, where N,N-diisopropylethylamine is preferred. By way of general guidance and depending on the base and solvent used, the reaction may be carried out at a temperature ranging from about 20° to 160° C., for about 1 to 20 hours, to form a compound of formula (II) or (III).

Step 4.

The present invention also provides a process for preparing a compound of formula (V):

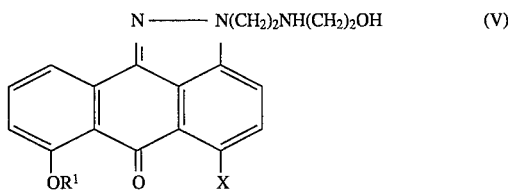

wherein

R$^1$ and X are as defined above;

comprising reacting a compound of formula (I), as defined above, with ethanolamine in a suitable solvent, optionally in the presence of a suitable base, to form a compound of formula (V). By way of general guidance and depending on the base and solvent used, the reaction may be carried out for about 6 to about 24 hours, at a temperature of about 20°–100° C. The base is preferably potassium carbonate.

The HCl salt form of the compound of formula (V), designated as the compound of formula (Vb), may be prepared by reaction of a compound of formula (V) with HCl gas in a solvent mixture, for example, a solvent mixture of an alcohol and a suitable solvent. By way of general guidance, the reaction may be carried out at a temperature of about −10° to about 30° C. for about 1–24 hours, to form a compound of formula (Vb) (the HCl salt form of the compound of formula (V). Other pharmaceutically acceptable salt forms of the compound of formula (V) may also be prepared.

Step 5.

The present invention also provides a process for the synthesis of an antineoplastic compound of formula (VI), such as losoxantrone ($R^1$=H), comprising the reaction of a compound of formula (V) or a pharmaceutically acceptable salt form thereof such as (Vb), with 2-(2-aminoethylamino)ethanol, optionally in the presence of a suitable base, in a suitable solvent, to form a compound of formula (VI) or a pharmaceutically acceptable salt form thereof, such as (VIb). The base and solvent is preferably pyridine. By way of general guidance and depending on the base and solvent used, the reaction may be carried out at a temperature ranging from about 60° C. to the boiling temperature of the solvent, for about 6 to 24 hours, to form the compound of formula (VI), or a pharmaceutically acceptable salt form thereof.

The present invention also provides processes for preparing a compound of formula (V):

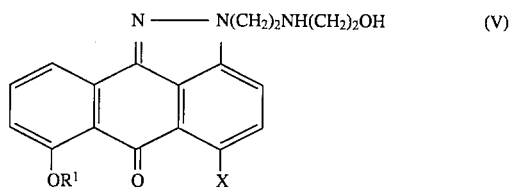

or a pharmaceutically acceptable salt thereof, wherein $R^1$ is 2,4,6-trimethylbenzyl and X is Cl;

comprising the steps of:
(1) reacting a compound of formula (II):

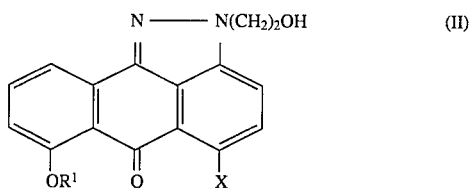

or a pharmaceutically acceptable salt thereof, wherein $R^1$ and X are as defined above;

with a brominating, chlorinating, or iodinating agent in a suitable solvent; and (2) reacting the reaction product from step (1) with ethanolamine, to form the compound of formula (V).

The brominating, chlorinating, or iodinating agent in step (1) above may be selected from any of a variety of such agents known in the art of synthetic organic chemistry, for example but not limited to, triphenylphosphine/carbontetrabromide, HBr, diphos-$Br_2$, N-bromosuccinimide (NBS), thionyl bromide, triphenylphosphine/carbontetrachloride, and thionyl chloride. By way of general guidance and depending on the solvent and brominating, chlorinating, or iodinating agent used, the reaction may be carried out at a temperature of about 10° to 60° C., for about 10 to 120 min. The reaction with ethanolamine of step (2) may be carried out at about 20° to 100° C., for about 2 to 48 h, to from the compound of formula (V).

Generally, pharmaceutically acceptable salts of the compounds produced by the methods of the invention can be prepared by reacting the free base form of these compounds with a stoichiometric amount of the appropriate acid in an organic solvent. Lists of suitable salts are found in "Remington's Pharmaceutical Sciences", 17th ed., Mack Publishing Company, Easton, PA, p.1418 (1985), the disclosure of which is hereby incorporated herein by reference.

Scheme 1 below describes the overall reaction sequence for the preparation of the desired compound of formula (VI), and pharmaceutically acceptable salt forms thereof.

Scheme 1.

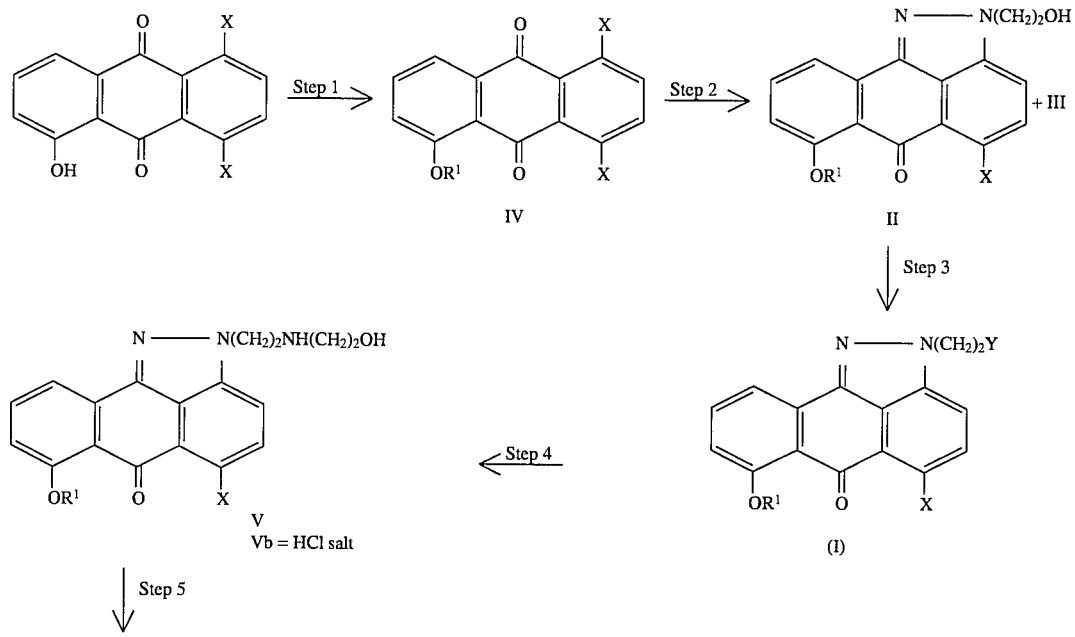

-continued
Scheme 1.

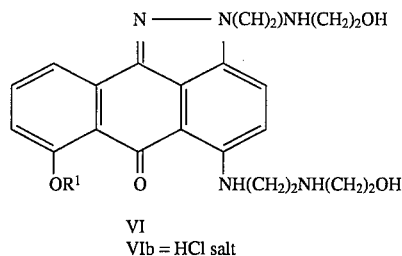

VI
VIb = HCl salt wherein $R^1$, X and Y have the meanings given above

It is therefore an object of the present invention to provide an improved process for the preparation of losoxantrone and other antineoplastic agents of formula (VI).

Step 1.

In Step 1 of the reaction scheme shown above the starting material has the formula:

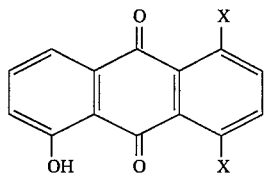

wherein X is defined as above for formula (I). Reaction of this starting material with hydroxyl protecting group reagent in a suitable solvent, optionally in the presence of base, provides a compound of formula (IV), wherein $R^1$ is a hydroxyl protecting group. For example, reaction of the starting material with a benzyl halide, such as 2,4,6-trimethylbenzyl chloride, provides a compound of formula (IV) wherein $R^1$ is benzyl or substituted benzyl group. As discussed above $R^1$ can be any of many other protecting groups used for hydroxyl as is appreciated by one of skill in the art of organic synthesis. Therefore, one skilled in the art may refer to the text "Protective Groups in Organic Synthesis", Green and Wuts, John Wiley & Sons, 1991, foe the selection of other possible protecting groups that could be utilized for the purpose of the present invention.

The reaction of Step 1 may be conducted in a suitable solvent or mixture of solvents, for example, acetone and dimethyl formamide or acetone and dimethyl acetamide. By way of general guidance and depending on the solvent and hydroxyl protecting group reagent used, the reaction may be carried out at a temperature ranging from about 22° to 80° C., preferably about 65° C. The reaction is conducted in an inert atmosphere such as nitrogen. The compound of formula (IV) can be separated from the reaction mixture upon cooling and used in Step 2 without further purification.

In Step 2, compounds of formulas (II) and (III) are prepared as a mixture of regioisomers (about 4/1 ratio and 85% yield) by the reaction of a compound of formula (IV) with 2-hydroxyethylhydrazine in a suitable aprotic solvent, for example, tetrahydrofuran, N,N-dimethylformamide, dimethyl sulfoxide, or N,N-dimethylacetamide, preferably, N,N-dimethylacetamide. The reaction may be conducted at a temperature ranging from about 20° to 160° C., preferably about 80° C. The reaction is preferably carried out in the presence of a suitable base, for example, potassium carbonate, sodium carbonate, N,N-dimethylaminopyridine, triethylamine, diisopropyl ethylamine, preferably, diisopropylethylamine. The compounds of formulas (II) and (III) can be isolated by addition of this reaction mixture to water. The precipitate may be collected by a filtration, washed with water, ethyl acetate and hexane to provide a mixture of compounds of formulas (II) and (III) (regioisomers) which can be used in the next reaction without further purification.

In Step 3, novel compounds of formula (I) were prepared by the reaction of the mixture of regioisomers of formulas (II) and (III) with a reagent suitable to convert a hydroxyl group to a leaving group, such as $ClSO_2R^2$. Such reagent suitable to convert a hydroxyl group to a leaving group can be selected from a variety of such reagents as will be appreciated by one of skill in the art of organic synthesis. Such reagents may be selected from, for example, benzenesulfonyl chloride, dimethylbenzenesulfonyl chloride, trimethylbenzene sulfonyl chloride, chlorobenzenesulfonyl chloride, dichlorobenzenesulfonyl chloride, trichlorobenzenesulfonyl chloride, toluenesulfonyl chloride, preferably, toluenesulfonyl chloride (tosyl chloride).

As discussed above, a chlorinating agent such as thionyl chloride may also be used as such a reagent to provide Y=Cl. An essentially isomerically pure compound of formula (I) (99.5%) can be isolated by precipitation from a mixed solvent composed, for example, of methanol and methylene chloride, and such compound of formula (I) can be used in the next reaction without chromatographic separation.

For a compound of formula (I), if Y is chlorine, bromine, iodine or methanesulfonyloxy, a chromatographic separation is necessary in order to obtain isomeric purity.

The reaction in Step 3 is optionally, but preferably carried out in the presence of a suitable base. Preferable suitable bases are pyridine and 1,8-diazabicyclo[5,4,0]undec-7-ene (DBU). For example, DBU produces yields significantly enriched in the desired tosyl substituted compound of formula (I) (a preferred embodiment) derived from the major isomeric alcohol of formula (II). DBU also yields the enriched form in a reaction time of about 3–5 hours. The base and the reagent suitable to convert the hydroxyl group to a leaving group, such as the tosyl reagent, may be employed in about 2–4 molar excess relative to the alcohol of formula (II); the reaction temperature is generally between about −15° C. and 30° C., a chilled solution.

Other suitable bases can be employed, such as 1,5-diazabicyclo[4,3,0]non-5-ene (DBN), 1,4-diazabicyclo[2,2,2]octane (DABCO), 4-dimethylamino pyridine (DMAP), or tetramethylethylenediamine (TMEDA). Generally, these improve the reaction time relative to pyridine but may lead to a mixture of isomeric blocked alcohols.

The reaction of Step 3 may also be carried out using thionyl chloride ($SOCl_2$) in a suitable solvent, in the presence of a suitable base, to form a compound of formula (I) wherein Y=Cl. This reaction may be carried out at a temperature of about 10°–50° C. for 1–24 h to form a compound of formula (I) where $R^1$ is defined as above and X and Y are Cl.

In Step 4, compounds of formula (Vb) (HCl salt) can be prepared by the reaction of formula (I) with ethanolamine to give compounds of formula (V), followed by treatment with HCl.

In Step 5, a compound of formula (V) or (Vb) is reacted with 2-(2-aminoethylamino)ethanol in a suitable solvent, such as pyridine, followed by conversion into the dihydrochloride salt form to provide a compound of formula (VI), such as losoxantrone (where $R^1$=H).

The synthetic processes of the present invention can also be employed for the synthesis of other antineoplastic agents as disclosed in G. Zagotto et al., Bioorganic & Medicinal Chemistry, 2(7), 1992, p659; H. D. H. Showalter et al., J. Med. Chem., 27, 1984, p255; H. D. H. Showalter et al. J. Med. Chem., 30, 1987, p121; W. R. Leopold, Cancer Research, 45, 1985, p5532; V. G. Beylin et al., J. Heterocyclic Chem., 26, 1989, p85; U.S. Pat. No. 4,556,654; EP 0103381. The disclosure of each of these references is hereby incorporated herein by reference.

The following examples are meant to be illustrative of the present invention. These examples are presented to exemplify the invention and are not to be construed as limiting the invention's scope.

Using the procedures described above and outlined in Scheme 1, the following compounds of formula (I) were prepared.

EXAMPLE 1

1,4-Dichloro-5-[(2,4,6-trimethylphenyl)methoxy]-9, 10-anthracenedione (formula (IV) wherein X=Cl and R1=2,4,6-trimethylbenzyl).

STEP 1

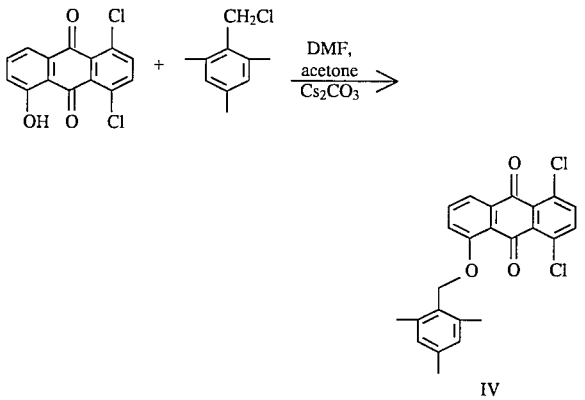

A 4-necked round bottom flask (1.0 L) equipped with a mechanical stirrer, thermometer and a condenser with a nitrogen bubbler was purged with nitrogen for 10 min. This flask was charged with 1,4-dichloro-6-hydroxy-9,10-anthracenedione (220.0 g, 0.75 mol), cesium carbonate (164.0 g, 0.5 mol), 2,4,6-trimethylbenzyl chloride (180.0 g, 1.0 mol), acetone (2.8 L) and N,N-dimethylformamide (0.9 L). The mixture was heated to reflux (65° C.) under nitrogen (1 atm) for 10 h, and then cooled to room temperature (22° C.) and stirred for 16 h. The reaction mixture which resulted was cooled to 0° C. and kept at that temperature for 2 h. The precipitate was collected by filtration, washed with warm water (50° C., 2×400 mL), methanol (2×120 mL) and dried in a vacuum oven (50° C., 10 mm) for 20 h to provide the desired product IV (311.8 g, 98% yield). mp 220°–222° C. CI mass spectrum m/e 425 (M+1).

EXAMPLE 2

5-Chloro-2-(2-hydroxyethyl)-7-[(2,4,6-trimethylphenyl)methoxy]anthra-[1,9-cd]pyrazol-6 (2H)-one; formula (II) and 5-Chloro-2-(2-hydroxyethyl)-10-[(2,4,6-trimethylphenyl)methoxy]anthra-[1,9-cd]pyrazol-6(2H)-one, formula (III).

STEP 2

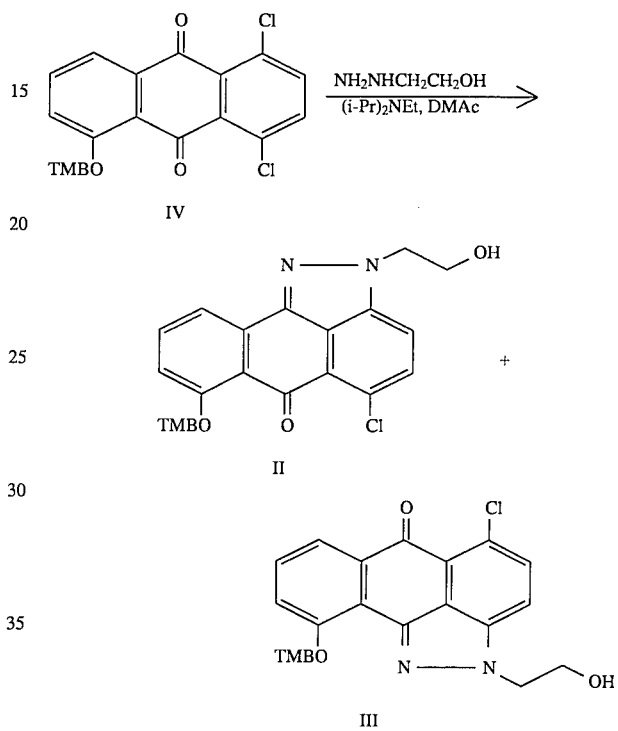

A 4-necked round bottom flask (12.0 L) equipped with a mechanical stirrer, a nitrogen gas-inlet tube, and a condenser with bubbler was charged with IV (304.0 g, 0.72 mol) and DMAc (1.8 L). The mixture was heated to 80° C., and the solution of 2-hydroxyethylhydrazine (175.0 g, 2.23 mol), N,N-diisopropylethylamine (182.0 g, 1.4 mol) and DMAc (1.7 L) was added over a three hour period. The mixture which resulted was stirred at 80° C. for additional 4 h, and then at 30° C. for 16 h. The reaction mixture was cooled to room temperature and then slowly added to water (7.2 L). The precipitate was collected by filtration, washed with water (2×1.0 L), cold ethyl acetate (2×1.0 L) and hexane (1.0 L). The solid was dried in a vacuum oven (40° C., 10 mm) for 24 h to provide the desired products II and III (269.0 g, ratio of II to III: 80/20, 85% yield). mp. 200°–203° C.; HPLC-CI-MASS m/e 447 (M+I).

EXAMPLE 3

5-Chloro-2-[2-[[(4-methylphenyl)sulfonyl]oxy] ethyl]-7-[(2,4,6-trimethylphenyl)methoxy]anthra-[1, 9-cd]pyrazol-6(2H)-one, formula (I).

STEP 3

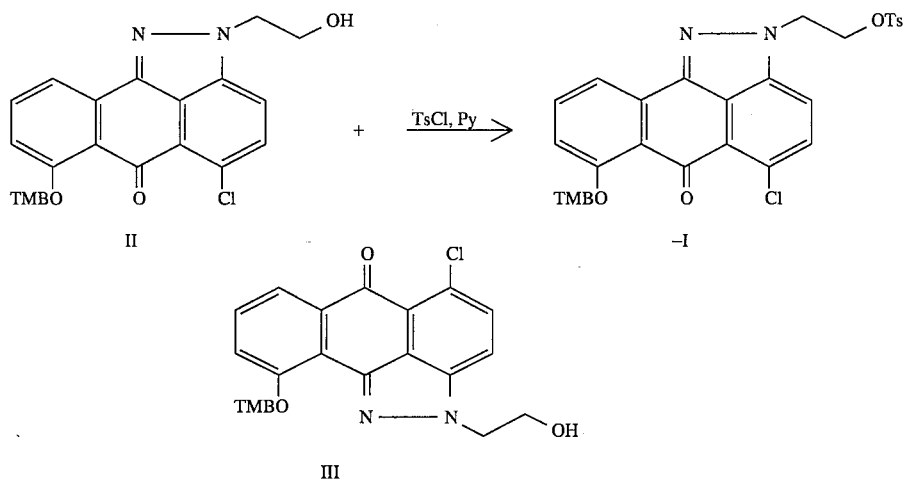

A 4-necked round bottom flask (2.0 L) equipped with a mechanical stirrer, thermometer and a condenser with a nitrogen bubbler was purged with nitrogen for 10 min. The flask was charged with the mixture of II and III (100.0 g, 0.22 mol), methylenechloride (1.0 L) and pyridine (Py) (54.0 g, 0.68 mol). The mixture which resulted was cooled to 0° C., and p-toluenesulfonyl chloride (TsCl) (84.0 g, 0.44 mol) was slowly added over a 25 min period. The mixture was stirred at room temperature for 48 h, and an additional portion of p-toluenesulfonyl chloride (21.0 g, 0.11 mol) was added. The mixture which resulted was stirred at room temperature for 10 h and methylene chloride (2.0 L) was added. The mixture was filtered and the filtrate was washed with water (2×0.8 L) and brine (0.5 L). The organic layer was dried ($K_2CO_3$), and the solvent was removed under reduced pressure. The residue was solidified by adding a mixed solvent of methanol and methylene chloride (0.6 L, 2/1 ratio), and cooled to 4° C. for 4 h. The precipitate was filtered, washed with mixed solvent of methanol and methylene chloride (3×20 mL, 2/1 ratio) and dried (40° C., 10 mm) for 20 h to provide the desired product I (89.4 g, 99.5 A% peak purity, 83% yield based on 80% purity of desired isomer in starting material). mp. 180°–183° C.

EXAMPLE 3A

This relates to Step 3, as described in Example 3, except using DBU instead of pyridine. Fourteen grams of a mixture of the alcohols of formula (II) and (III) was charged to a 1 L, 3 necked round bottom vessel (74 A% of the major regioisomer, 0.74×31.22 mmol=23.1 mmol). 1.8-diazabicyclo[5,4,0]undec-7-ene (DBU) was charged (3.5×31.22 mmol DBU 98% Aldrich=16.974 g) rinsed in with 140 mL of methylene chloride. The reaction slurry was stirred mechanically then cooled down to −12° C. with an ice/methanol bath. p-Toluenesulfonyl chloride (Aldrich 98%) was charged to the reaction mixture (3.5×31.22 mmol=21.26 g). The reaction temperature rapidly rose to 7° C. then cooled to 0° C. (3 min total). The cooling bath was removed and the reaction allowed to warm to room temperature over 50 min then aged at room temp for 3 h, 11 min. Methylene chloride 560 mL. was added to the reaction mixture and stirred 0.5 h and then the reaction was filtered using a fritted funnel and the precipitate and reaction vessel was washed with 140 mL methylene chloride. The solid was suction dried under high vacuum giving 1.7 g of starting alcohol (III) (minor isomer) identified by HPLC (12.1% of sm.). The filtrate was transferred to the clean reaction vessel mixed with 140 mL. of methanol. The reaction mixture was heated distilling out the methylene chloride till the pot temp. reached 52° C. causing the precipitation of the product. The solids were filtered off on a fritted filter then washed and rinsed with 280 mL of methanol at room temperature, then sunction dried and dried under high vacuum at 45°–50° C. The desired tosylated isomer product (I) weighed 10.44 g (75.2% isolated yield based on 74% purity of desired isomer in starting material) and did not contain the minor tosyl isomer by HPLC (98.69 A% peak purity). No additional desired tosyl isomer was detected in the mother liquors.

EXAMPLE 4

5-Chloro-2-[2-[(2-hydroxyethyl)amino]ethyl]-7-[(2, 4,6-trimethylphenyl)methoxy]anthra-[1,9-cd]pyrazol-6 (2H)-one, formula (Va)

STEP 4

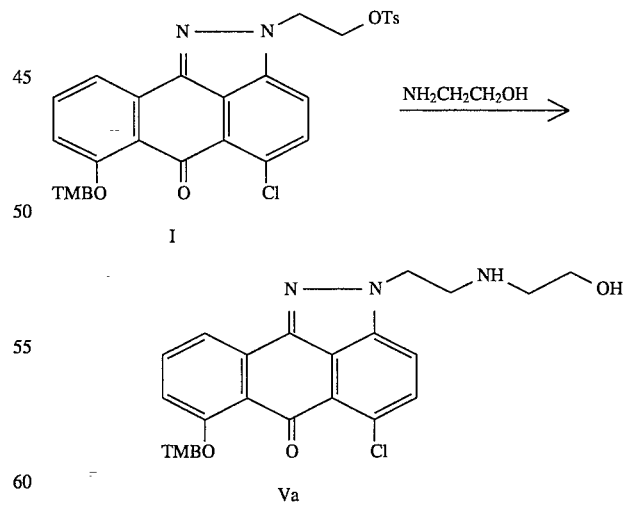

A 4-necked round bottom flask (1.0 L) equipped with a mechanical stirrer, thermometer and a condenser with a nitrogen bubbler was purged with nitrogen for 10 min. This flask was charged with I (75.0g, 0.12 mol), DMAc (0.7 L), ethanolamine (30.0 g, 0.49 mol) and potassium carbonate (26.0 g, 0.19 mol). The mixture was stirred at 45° C. for 18 h, cooled to room temperature and then added to ice water (4° C., 2.0 L). This mixture was kept at room temperature for 18 h and filtered. The solid was washed with water (2×0.2 L), hexane (0.2 L) and dried (40° C., 20 mm) for 20 h to furnish (Va) (55.5 g, 91% yield). mp 177°–9° C.; CI-MS m/e 490 (M+1).

EXAMPLE 5

5-Chloro-2-[2-[(2-hydroxyethyl)amino]ethyl]-7-[(2,4,6-trimethylphenyl)methoxy]anthra-[1,9-cd]pyrazol-6 (2H)-one hydrochloride (HCl salt, Vb).

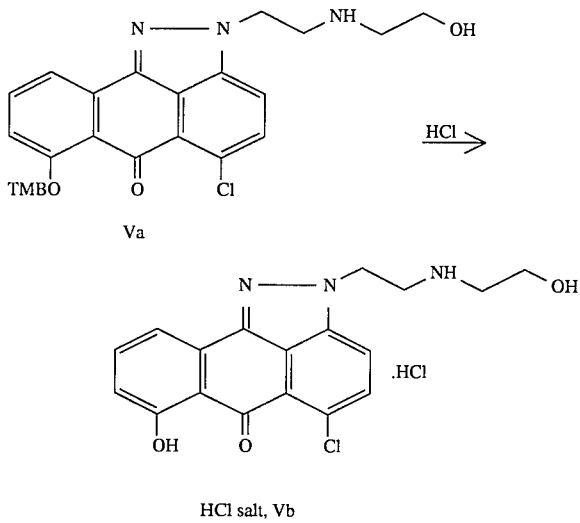

A 4-necked round bottom flask (1.0 L) equipped with a mechanical stirrer, thermometer, HCl-inlet tube and a condenser was charged with Va (54.5 g, 0.11 mol) and a mixed solvent of methanol and methylene chloride (0.51 L, 1/4 ratio). The solution was cooled to 0° C. and HCl (gas) was bubbled through the solution. When the temperature rose to 20° C. the bubbling was stopped and the mixture was cooled to 5° C. The reaction mixture was sealed with rubber septums after this process was repeated three times. This mixture was allowed to warm up to room temperature and stirred for 16 h. Nitrogen was bubbled through the mixture for 20 min, and the precipitate was collected by a filtration, washed by methylene chloride (2×0.4 L) and hexane (0.8 L) to provide the desired product (43.3 g, 100% yield). mp 245°–250° C.

EXAMPLE 6

Losoxantrone

STEP 5

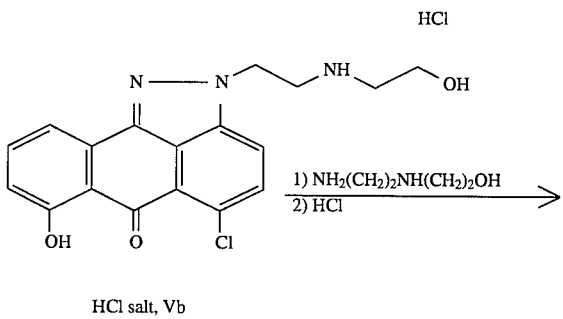

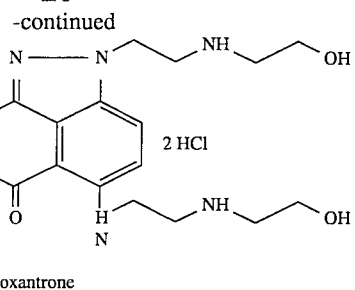

Losoxantrone

A 4-necked round bottom flask (1.0 L) equipped with a mechanical stirrer, thermometer and a condenser with a nitrogen bubbler was purged with nitrogen for 10 min. This flask was charged with the HCl salt of Vb (40.0 g, 0.10 mol), 2-(2-aminoethylamino)ethanol (104 g, 1.00 mol) and pyridine (0.2 L). This mixture was stirred under nitrogen (1 atm) at 82° C. for 18 h and then cooled to room temperature. To this mixture 2-propanol (0.3 L) was added and the mixture which resulted was stirred at 5° C. for 4 h. The precipitate was filtered, washed with cold isopropanol (2×0.2 L) and hexane (2×0.2 L). The solid was dissolved in methanol (1.0 L) and the solution of HCl-isopropanol (6 N, 50 mL) was added. The mixture was stirred at room temperature for 10 min and then heated to reflux (65° C.) for 10 min. This mixture was cooled and stirred at 0° C. for 2 h. The red-orange precipitate was filtered, washed with cold methanol (4×150 mL), hexane (2×250 mL) and dried (60° C., 20 mm) to provide Losoxantrone (27.7 g, 55% yield). mp 268°–270° C.

EXAMPLE 7

One-pot preparation (PPh$_3$/CBr$_4$, ethanolamine) of 5-Chloro-2-[2-[(2-hydroxyethyl)amino]ethyl]-7-[(2,4, 6-trimethylphenyl)methoxy]anthra-[1,9-cd] pyrazol-6(2H)-one, formula (V).

A 3-necked round bottom flask (500 mL) equipped with a magnetic stirrer, a nitrogen bubbler, and a condenser was charged with the regioisomers of TMB-hydroxyethyl pyrazol II and III (10.0 g, 94%, 21.0 mmol), triphenylphosphine (99%, 11.4 g, 43.0 mmol) and dichloromethane (dry, 200 mL). The solution was stirred under nitrogen (1 atm) at room temperature for 10 min, and carbon tetrabromide (7.2 g, 99%, 21.5 mmol) was added in one portion (temperature increase around 10 degrees). The mixture which resulted was stirred under nitrogen (1 atm) at r.t. for 1 h and then at 40° C. for 10 min (all starting materials should be converted into their corresponding bromides at this point). The reaction mixture was cooled back to room temperature, and ethanolamine (10.0 g, 99%, 162.1 mmol) was added in one portion. The mixture which resulted was stirred under nitrogen (1 atm) at 40° C. for 24 h. The solvent was removed under reduced pressure, and the residue was washed with ethyl acetate (100 mL) and filtered. The solid was washed with hexane and dried under nitrogen (60° C., 20 mm) for 60 h to provide the desired product Va and its regioisomer (100% yield).

EXAMPLE 8

5-Chloro-2-(2-chloroethyl)-7-[(2,4,6-trimethylphenyl)methoxy]anthra-[1,9-cd]pyrazol-6(2H) one, formula (I).

A 3-necked round bottom flask (250 mL) equipped with a magnetic stirrer, a nitrogen gas-inlet tube, and a condenser with bubbler was charged with the mixture of regioisomers 5-chloro-(2-hydroxyethyl)-7-[2,4,6-trimethylphenyl)methoxy]anthra-[1,9-cd]pyrazole-6 (2H) one II and 5-chloro-2-(2-hydroxyethyl)-10-[(2,4,6-trimethylphenyl)methoxy]anthra-[1,9-cd]pyrazol-6(2tt)- one III (5.0 g, 94%, 10.1 mmol), pyridine (1.6 g, 20.0 mmol) and acetonitrile (dry, 100 mL). The mixture which resulted was cooled to 0° C. To this mixture was added thionyl chloride in dichloromethane (2M, 7 mL). The mixture was stirred at r.t. for 6 h, and the reaction was monitored by HPLC every three hours. After completion, the reaction was quenched by the addition of water (100 mL) at 0° C. The residue was dissolved in ethyl acetate (300 mL) and the layers were separated. The organic layer was washed with water (50 mL), sodium bicarbonate (5%, 50 mL), brine (50 mL) and dried (MgSO$_4$). The solvent was removed under reduced pressure and the residue (4.9 g) was chromatographed on flash silica gel (400 g, EtOAc/Hexane from 20:80 to 50:50) to provide the desired regioisomer I (0.7 G). MS (CI) m/e 465 (M+1).

EXAMPLE 9

5-Chloro-2-[2-[[(2-chlorobenzene) sulfonyl]oxy] ethyl]-7-[(2,4,6-trimethylphenyl)methoxy]anthra-[1,9-cd]pyrazol-6(2H)-one, formula (I)

Starting with 2-chlorobenzenesulfonyl chloride and the mixture of regioisomers of 5-chloro-2-(2-hydroxyethyl)-7-[(2,4,6-trimethylphenyl)methoxy]anthra-[1,9-cd]pyrazol-6(2H)-one (II) and 5-chloro-2-(2-hydroxyethyl)-10-[(2,4,6-trimethylphenyl)methoxy]anthra-[1,9-cd]pyrazol-6(2H)-one (III), using the procedure of example 3, the title compound was prepared.

EXAMPLE 10

5-Chloro-2-[2-[[(3-chlorobenzene) sulfonyl]oxy] ethyl]-7-[(2,4,6-trimethylphenyl)methoxy]anthra-[1,9-cd]pyrazol-6(2H)-one, formula (I)

Starting with 3-chlorobenzenesulfonyl chloride and the mixture of regioisomers of 5-chloro-2-(2-hydroxyethyl)-7-[(2,4,6-trimethylphenyl)methoxy]anthra-[1,9-cd]pyrazol-6(2H)-one (II) and 5-chloro-2-(2hydroxyethyl)-10-[(2,4,6-trimethylphenyl)methoxy]anthra-[1,9-cd]pyrazol-6(2H)-one (III), using the procedure of example 3, the title compound was prepared.

EXAMPLE 11

5-Chloro-2-[2-[(benzenesulfonyl)oxy]ethyl]-7-[(2,4,6-trimethylphenyl)methoxy]anthra-[1,9-cd]pyrazol-6-(2H) one, formula (I)

Starting with benzenesulfonyl chloride and the mixture of regioisomers of 5-chloro-2-(2-hydroxyethyl)-7-[(2,4,6-trimethylphenyl)methoxy]anthra-[1,9-cd]pyrazol-6(2H)-one II and 5-chloro-2-(2-hydroxyethyl)-10-[(2,4,6-trimethylphenyl) methoxy]anthra-[1,9-cd]pyrazol-6(2H)-one III, using the procedure of example 3, the title compound was prepared.

EXAMPLE 12

5-Chloro-2-[2-[(methanesulfonyl) oxy]ethyl]-7-[(2,4,6-trimethylphenyl)methoxy]anthra-[1,9-cd]pyrazol-6 (2H) one, formula (I)

Starting with methanesulfonyl chloride and the mixture of regioisomers of 5-chloro-2-(2-hydroxyethyl)-7-[(2,4,6-trimethylphenyl)methoxy]anthra-[1,9cd]pyrazol-6-(2H)-one II and 5-chloro-2-(2-hydroxyethyl)-10-[(2,4,6-trimethylphenyl) methoxy]anthra-[1,9-cd]pyrazol- 6(2H)-one III, usiong the procedure of example 3, the title compound was prepared.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A process for preparing a compound of formula (V):

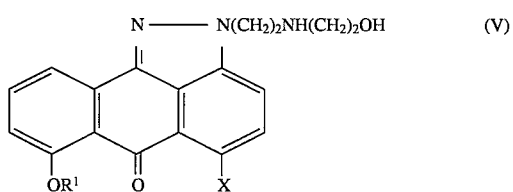

or a pharmaceutically acceptable salt form thereof, wherein:
x is selected from:
 (a) F, Cl, Br, I,
 (b) methanesulfonyloxy,
 (c) toluenesulfonyloxy,
 (d) trifluoromethanesulfonyloxy, or
 (e) —OH;
$R^1$ is selected from:
 (a) benzyl substituted with 0–3 $R^5$;
 (b) naphthylmethyl substituted with 0–3 $R^5$;
 (c) anthrylmethyl substituted with 0–3 $R^5$; or
 (d) $C_1$–$C_4$ alkyl; or
 (e) H;
$R^5$ is independently selected from: $C_1$–$C_4$ alkyl, halogen, $OR^6$, $NO_2$; and
$R^6$ is independently selected from: H, $C_1$–$C_8$ alkyl, $C_2$–$C_6$ alkenyl, $C_3$–$C_8$ cycloalkyl, $C_4$–$C_8$ cycloalkylmethyl, $C_6$–$C_{10}$ aryl, or $C_7$–$C_{11}$ arylalkyl;
comprising the steps of:
(1) reacting a compound of formula (IV):

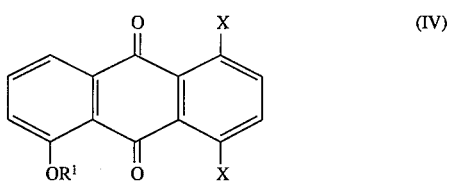

wherein:
$R^1$ and X are as defined above;
with 2-hydroxyethylhydrazine, in a suitable solvent, in the presence of a base, to form a mixture of regioisomers of formula (II) and formula (III) in which the ratio of (II) to (III) is about 4 to 1:

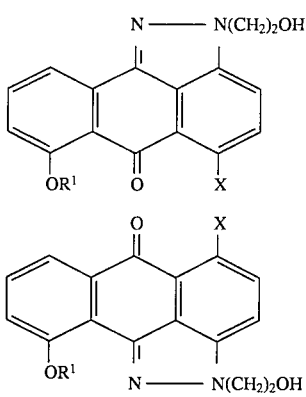

(II)

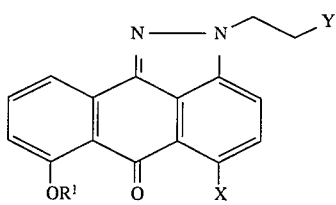

(III)

wherein $R^1$ and X are as defined above;

(2) reacting the mixture of regioisomers (II) and (III) with $ClSO_2R^2$, wherein:

$R^2$ is selected from:
(a) $C_vF_{2v+1}$ where v is 1 to 4, or
(b) phenyl or phenyl optionally substituted with from 1 to 3 of the groups selected from Cl, F, Br, $NO_2$ or $CH_3$;

said reaction being carried out in a suitable solvent, in the presence of a suitable base, followed by precipitation with an alcohol or a mixture of methylene chloride and methanol to provide a single isomer of formula (I):

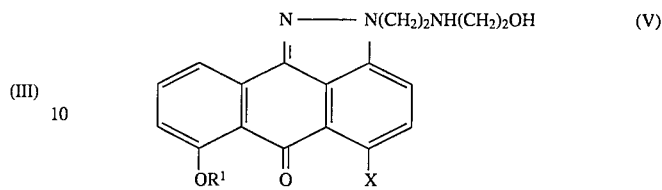

(I)

wherein Y is $-OSO_2R^2$ and $R^1$ and X are as defined above;

(3) reacting the compound of formula (I) with ethanolamine in a suitable solvent in the presence of a suitable base, to form a compound of formula (V):

wherein $R^1$ and X are as defined above.

2. A process of claim 1 wherein X is Cl, Br or I.

3. A process of claim 2 wherein X is Cl and Y is toluensulfonyloxy.

4. A process of claim 3 in which, in step (2), the base is 1,8-diazabicyclo[5.4.0]undec-7-ene (DBU) and the reaction is carried out at a temperature ranging from about −10° C. to 10° C., for about 2 to 7 hours.

5. A process of claim 3 in which, in step (2), the base is pyridine and the reaction is carried out at a temperature ranging from about −10° C. to 20° C., for about 24 to 60 hours.

6. A process of claim 4 in which, in step (2), the precipitation solvent for generating the single isomer of formula (I) is methylene chloride and methanol.

7. A process of claim 5 in which, in step (2), the precipitation solvent for generating the single isomer of formula (I) is methylene chloride and methanol.

* * * * *